United States Patent
Schoeppe et al.

(10) Patent No.: US 8,602,715 B2
(45) Date of Patent: Dec. 10, 2013

(54) DEVICE FOR STORING AND PROVIDING OBJECTS HAVING STANDARDIZED DIMENSIONS

(75) Inventors: Torsten Schoeppe, Jena (DE); Sebastian Eck, Jena (DE); Heiko Oehme, Jena (DE); Swen Tyrasa, Eineborn (DE); Patrick Hoost, Jena (DE); Jochen Eckardt, Jena (DE); Thomas Moore, Drackendorf (DE)

(73) Assignee: Cybio AG, Jena (DE)

( * ) Notice: Subject to any disclaimer, the term of this patent is extended or adjusted under 35 U.S.C. 154(b) by 381 days.

(21) Appl. No.: 12/979,412

(22) Filed: Dec. 28, 2010

(65) Prior Publication Data
US 2012/0057957 A1 Mar. 8, 2012

(30) Foreign Application Priority Data
Sep. 6, 2010 (DE) ............... 20 2010 012 318 U

(51) Int. Cl.
*G11B 17/12* (2006.01)
*G11B 23/00* (2006.01)
*B65G 59/06* (2006.01)

(52) U.S. Cl.
USPC ........ 414/795.3; 414/798.1; 221/11; 221/297

(58) Field of Classification Search
USPC .......... 221/11, 222; 369/179, 201; 414/795.4, 414/795.8, 796.1, 797.4, 797.5, 798, 798.1, 414/798.4, 798.5, 798.8; G9B/17.043
See application file for complete search history.

(56) References Cited

U.S. PATENT DOCUMENTS

| 3,517,482 | A | * | 6/1970 | Beninger ...................... 53/387.2 |
| 4,195,961 | A | * | 4/1980 | Waiblinger ................ 414/796.7 |
| 5,605,249 | A | * | 2/1997 | Gonyea ............................ 221/6 |
| 5,674,047 | A | * | 10/1997 | Lapeus et al. .............. 414/795.6 |
| 6,129,428 | A | | 10/2000 | Helwig |

(Continued)

FOREIGN PATENT DOCUMENTS

| DE | 19746455 C1 | 5/1999 |
| DE | 102005001888 A1 | 7/2006 |
| EP | 1332987 A2 | 8/2003 |
| WO | WO 9805753 A1 | 2/1998 |

OTHER PUBLICATIONS

ANSI/SBS Jan. 2004 "Footprint Dimensions", Jan. 2006.

(Continued)

*Primary Examiner* — Gregory Adams
(74) *Attorney, Agent, or Firm* — Leydig, Voit & Mayer, Ltd.

(57) ABSTRACT

A device for loading, storing and providing objects having standardized dimensions includes a storage unit with a carrier plate and four stackers. Each stacker includes a bottom surface disposed on top of the carrier plate. The stackers are configured to store objects stacked perpendicular to the carrier plate. The stackers are disposed symmetrically centered around a rotation axis that is perpendicular to the carrier plate and offset with respect to each other by an angle of 90°. A substructure is disposed underneath the carrier plate. An unloading device is configured to unload a selected object from a first of the stackers that is disposed in a transfer position. The storage unit is rotatable around the rotation axis so as to enable movement of each of the stackers into the transfer position.

8 Claims, 14 Drawing Sheets

(56) References Cited

U.S. PATENT DOCUMENTS

| | | | |
|---|---|---|---|
| 6,135,316 A * | 10/2000 | Wolfer et al. | 221/299 |
| 6,395,231 B1 | 5/2002 | Kraemer | |
| 6,558,110 B2 * | 5/2003 | Lu et al. | 414/798.1 |
| 7,214,022 B2 | 5/2007 | Melching | |
| 2002/0176803 A1 * | 11/2002 | Hamel et al. | 422/100 |
| 2004/0004415 A1 | 1/2004 | Melching | |
| 2008/0260511 A1 * | 10/2008 | Fattinger et al. | 414/788.1 |
| 2008/0272674 A1 | 11/2008 | Malin | |
| 2009/0026905 A1 | 1/2009 | Malin | |

OTHER PUBLICATIONS

RapidStak® system (Thermo Fischer), http:www.thermo.com/eThermo/CMA/PDFs/Product/productPDF_1133.pdf, downloaded Mar. 21, 2011.

Product information, Q-Stacker (model QR-210) Peak Robotics, Inc, downloaded Mar. 21, 2011.

Product information, Tomtec Quadra 3® (Tomtec, Hamden, CT, U.S.A.), downloaded Mar. 21, 2011.

* cited by examiner

- Prior art -

- Prior art -

- Prior art -

- Prior art -

- Prior art -

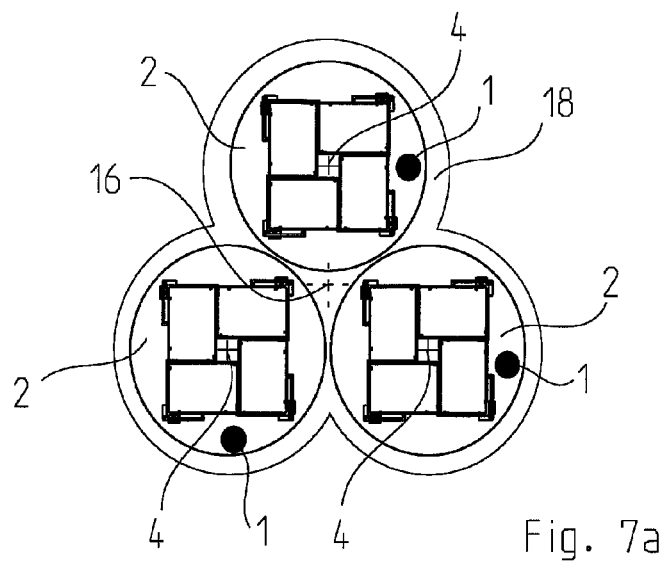
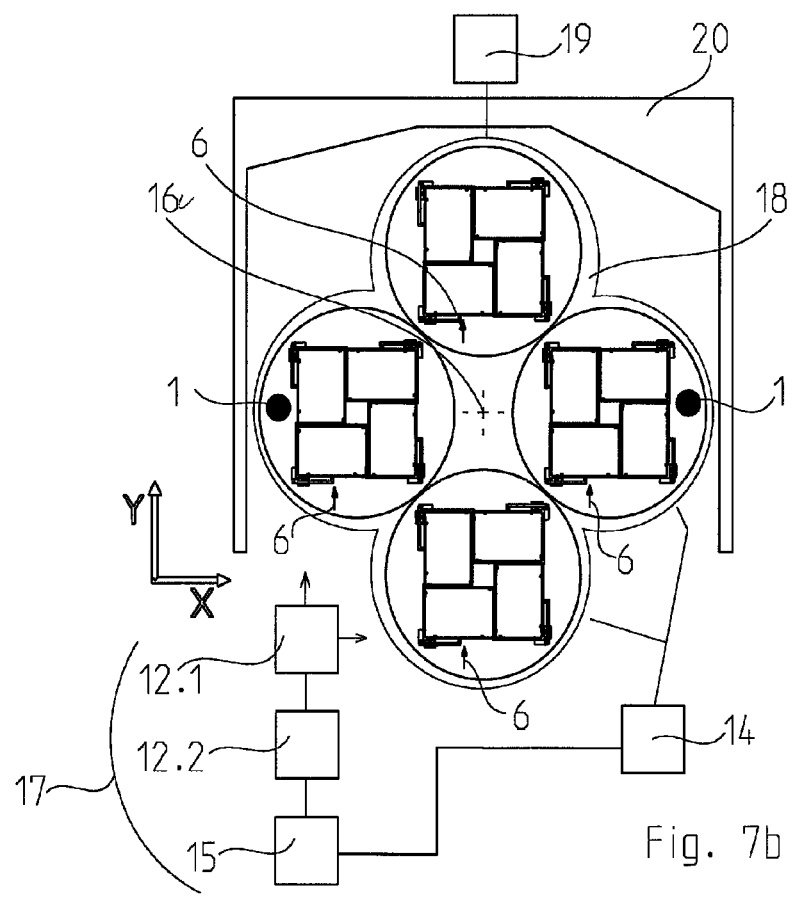

DEVICE FOR STORING AND PROVIDING OBJECTS HAVING STANDARDIZED DIMENSIONS

CROSS REFERENCE TO RELATED APPLICATIONS

This application claims priority to German Patent Application No. DE 20 2010 012 318.6, filed on Sep. 6, 2010, which is hereby incorporated by reference herein in its entirety.

FIELD

The invention relates to a device for storing and providing objects used in a laboratory and having standardized dimensions as well as to a chamber having such a device.

BACKGROUND

U.S. Pat. No. 6,395,231 describes a device for storing and providing objects having standardized dimensions. The applicant produces and sells such a device.

Since standardized well microplates that comply with U.S. standard ANSI/SBS 2-2004 "Footprint Dimensions" for microplates are employed to load and unload objects having standardized dimensions such as those used in many technical laboratory applications in the realm of research in molecular biology, biochemistry and molecular genetics as well as in medicine, biotechnology and diagnostics, conventional devices do not differ in terms of the shape and size of the footprint of the stackers, which are also referred to as racks or magazines. These standardized well microplates are plates having a standardized footprint size of 127.76 mm×85.48 mm. However, the device can also hold other standardized objects such as, for instance, containers for pipette tips, plates for storing specimens or else packaging units, for example, a well microplate with a lid, which is why the term "object" will be generally employed below. In order to accommodate as many objects as possible in the device, the objects are stacked and stored in a stacker, and as many such stackers as possible are arranged in a storage space in the device.

The stackers can contain storage compartments into each of which an object can be placed, so that these objects can be loaded or unloaded in any desired sequence using an unloading device (random access).

The objects can also be situated directly one above the other in a stacker, whereby the lowermost object rests on adjustable placement and separation elements ("separation elements" below) that are moved in order to transfer the lowermost object into an unloading device.

Two principles are typically employed for loading and unloading the stackers with objects. According to the so-called "first in, first out" (FIFO) principle, the first object to be loaded into a stacker is also the first to be unloaded again. A device that operates according to the FIFO principle is, for example, the Q-Stacker (model QR-210) made by PEAK ROBOTICS, INC.

The second principle is referred to as "last in, first out" (LIFO). In this case, the last objects to be loaded into a stacker are the first ones to be unloaded again. An example of this is the Tomtec Quadra 3® (Tomtec, Hamden, Conn., U.S.A.).

FIGS. 1a to 1g show an example of the procedure for loading an object 5 that is to be loaded into a stacker 3 according to the device described in U.S. Pat. No. 6,395,231.

The object 5 to be loaded is placed by means of an unloading device 12.1 located in an initial position beneath a bottom surface 3.2 of the stacker 3. An object 5 that is already present in the stacker 3 rests on a closed separation device 8 that is configured so that it can extend in a controlled manner and reversibly into the free cross section of the stacker 3. The object 5 present in the stacker 3 is held by the separation device 8 (FIG. 1a). The unloading device 12.1 brings the object 5 to be loaded into the stacker 3 from below in that the unloading device 12.1 is moved in the direction of the bottom surface 3.2 by means of a drive 12.2 of the unloading device (FIG. 1b). When the object 5 that is present is raised, latches 8.1 that can extend in a controlled manner and reversibly into the free cross section of the stacker 3 are magnetically retracted from the free cross section of the stacker 3, and the separation device 8 is opened (FIG. 1c). In this process, the two objects 5 come into contact with each other via a contact surface. The object 5 to be loaded is moved entirely into the stacker 3 by means of the unloading device 12.1. The object 5 that is already present in the stacker 3 is lifted by the object 5 that is to be loaded and by the unloading device 12.1, and then pushed further along the stacker 3 (FIG. 1d). The separation device 8 is then closed, as a result of which the latches 8.1 extend into the free cross section of the stacker 3 and underneath the two objects 5 (FIG. 1e). The unloading device 12.1 is moved downwards, as a result of which the two objects 5 are lowered in the stacker 3 until they come to rest on the latches 8.1 and are held by them (FIG. 1f). The unloading device 12.1 is moved back to its initial position, while the two objects 5 remain in the stacker 3 (FIG. 1g). An object 5 can be unloaded from the stacker 3 analogously.

According to U.S. Pat. No. 6,129,428 A, the stackers are arranged like a carrousel on a turntable. The individual stackers are oriented radially towards the outside. In order for an object to be unloaded from a storage compartment of a stacker, there is an unloading device that is configured here as a stationary lifting mechanism with a conveying platform that can be swiveled horizontally. Here, the appertaining stacker is rotated by the turntable towards the lifting mechanism to a transfer position, the conveying platform is moved to the height of the selected storage compartment and swiveled towards the storage compartment so that the object can be loaded or unloaded A drawback of the described carrousel-like arrangement of the stackers with respect to each other is that the ratio of the number of stackers to the required size of the turntable (below referred to as the density) worsens as the number of stackers increases.

A storage unit according to U.S. Pat. No. 7,214,022 B2 and U.S. Pat. Appl. No. 2004/0004415 A1 promises a higher density in that two parallel rows of storage slots are arranged on shelves on both sides of a passage in which a pick-up unit can be moved back and forth between transfer positions so that an object can be loaded or unloaded by means of the unloading device.

U.S. Pat. Appl. No. 2009/0026905 A1 and U.S. Pat. Appl. No. 2008/0272674 A1 describe a storage unit, especially for a climate controlled cabinet, in which several rows of parallel storage slots are arranged in a shelf, and the unloading device is configured in such a way that it can pick up a number of objects that matches the number of rows, so that in one transfer position, all of the objects located one behind the other are unloaded. A separation device then removes an object from the unloading device and the remaining objects are deposited once again. Such an approach further increases the density.

The RapidStak® system (Thermo Fischer) (http:www.thermo.com/eThermo/CMA/PDFs/Product/productPDF_1133.pdf; downloaded on Jun. 24, 2010) describes a device for storing and providing objects having standardized dimensions, wherein the objects are unloaded and dispensed from the stackers by means of an unloading and providing device at transfer positions that are each always associated with one stacker. The unloading and providing device can be moved in an x-y plane and can be brought to the transfer position of each stacker. In this context, the unloading and providing device is moved by means of a first module in the direction of the x-axis and of a z-axis that is perpendicular to the x-y plane, while the movement in the direction of the y-axis is effectuated by a second module that differs from the first module. With the approach according to The RapidStak® system, only the stackers that are arranged directly on the appertaining side can be loaded or unloaded from one side of the device. Consequently, in order for objects to be loaded in to or unloaded from the individual stackers, there has to be a great deal of access space at the side of and above The RapidStak® system. This, however, makes it very difficult to install and load the system in constricted spaces such as, for example, in a chamber.

The applicant designs, produces and sells a device that stores and dispenses objects having standardized dimensions and that serves as an accessory for pipetting systems such as, for instance, CyBi®-Well and JOBI-Well (FIG. 2).

The device described in U.S. Pat. No. 6,395,231 comprises a storage unit 1 having a carrier plate 2 and two vertical stackers 3 that are each arranged with their bottom surface 3.2 on the top of the carrier plate 2. A transfer position 6 (indicated by arrows) at an opening 7 is associated with each stacker 3, whereby the transfer positions 6 are oriented parallel to each other and facing in the same direction. Moreover, there is a substructure 11 on which the carrier plate 2 rests. There is also an unloading and providing device 12. One free wall 3.11 of each stacker 3 has a door 3.5 through which the stacker 3 can easily be loaded when said door is open.

Conventional devices have one stacker per transfer position, each of which has to be approached by an unloading device, as a result of which the cycle times that can be achieved are limited. Moreover, due to the different lengths of the movement distances that the unloading device has to travel to the various transfer positions, the cycle times also differ, which is disadvantageous from the standpoint of automation.

SUMMARY

In an embodiment, the present invention provides a device for loading, storing and providing objects that have standardized dimensions. The device includes a storage unit with a carrier plate and four stackers. Each stacker is configured to store objects stacked perpendicular to the carrier plate, each of the stackers includes a bottom surface disposed on top of the carrier plate. The stackers are disposed symmetrically centered around a rotation axis that is perpendicular to the carrier plate, and offset with respect to each other by an angle of 90°. A substructure is disposed underneath the carrier plate. An unloading device is configured to unload a selected object from a first of the stackers that is disposed in a transfer position. The storage unit is rotatable around the rotation axis so as to rotate each of the stackers into the transfer position.

PROVIDING BRIEF DESCRIPTION OF THE DRAWINGS

Exemplary embodiments of the present invention will be described in more detail below with reference to the drawings, in which:

FIG. 7a shows a schematic top view of another embodiment of a device in accordance with the invention having three storage units;

FIG. 7b shows a schematic top view of another embodiment of a device in accordance with the invention having four storage units;

DETAILED DESCRIPTION

Figure 1A:
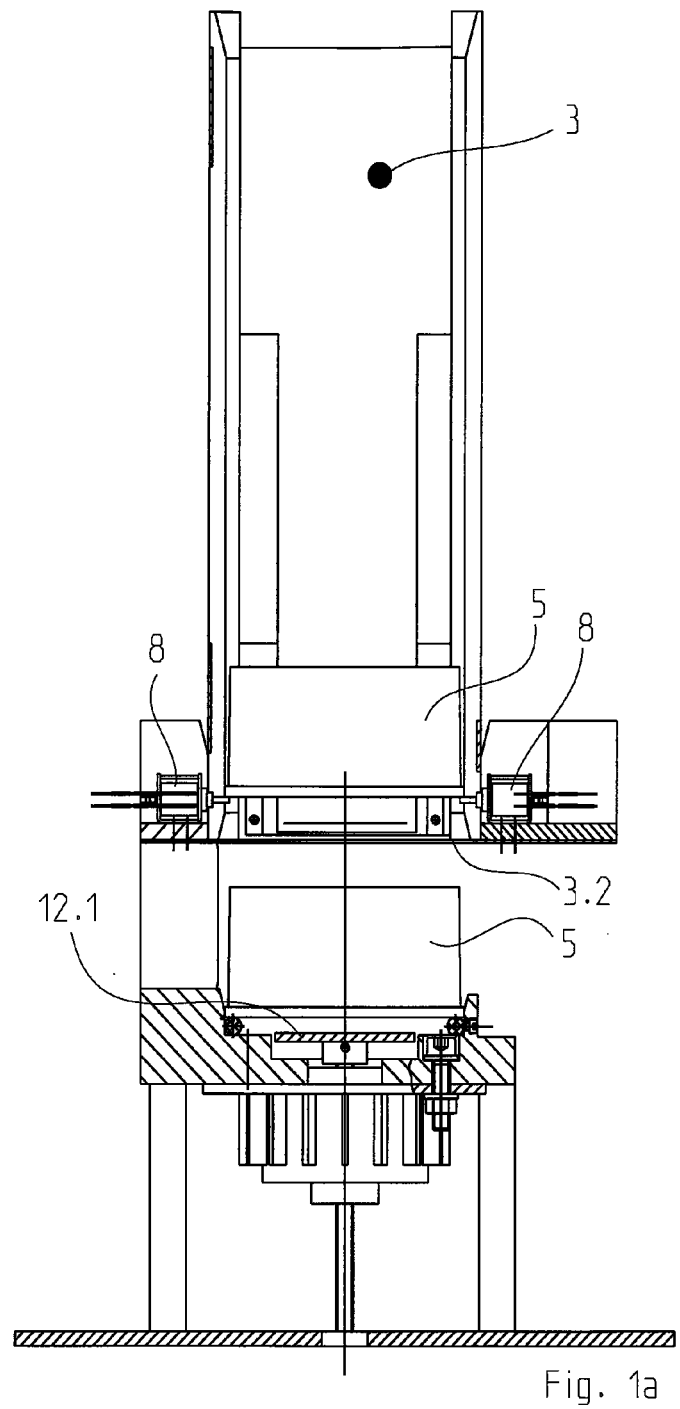
FIGS. 1a to 1g show a sequential depiction of an object being loaded into a conventional stacker.
Figure 1B:
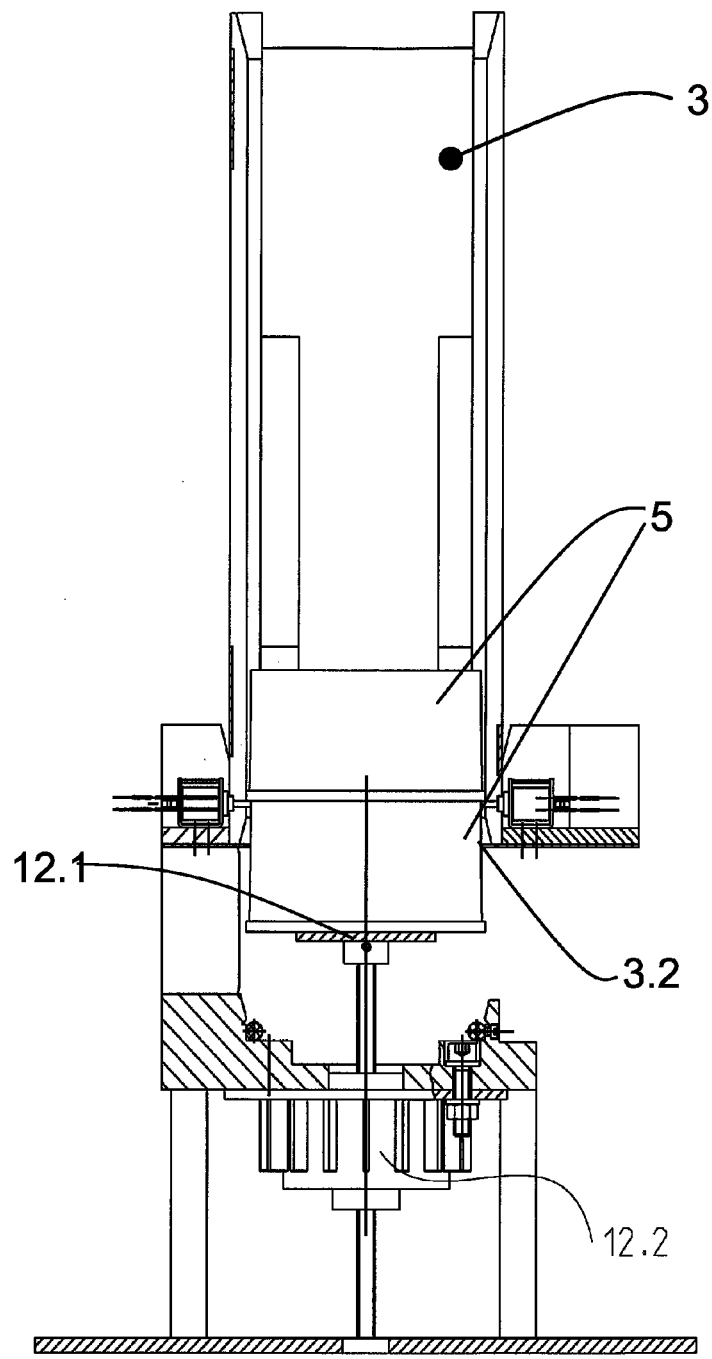
Figure 1C:
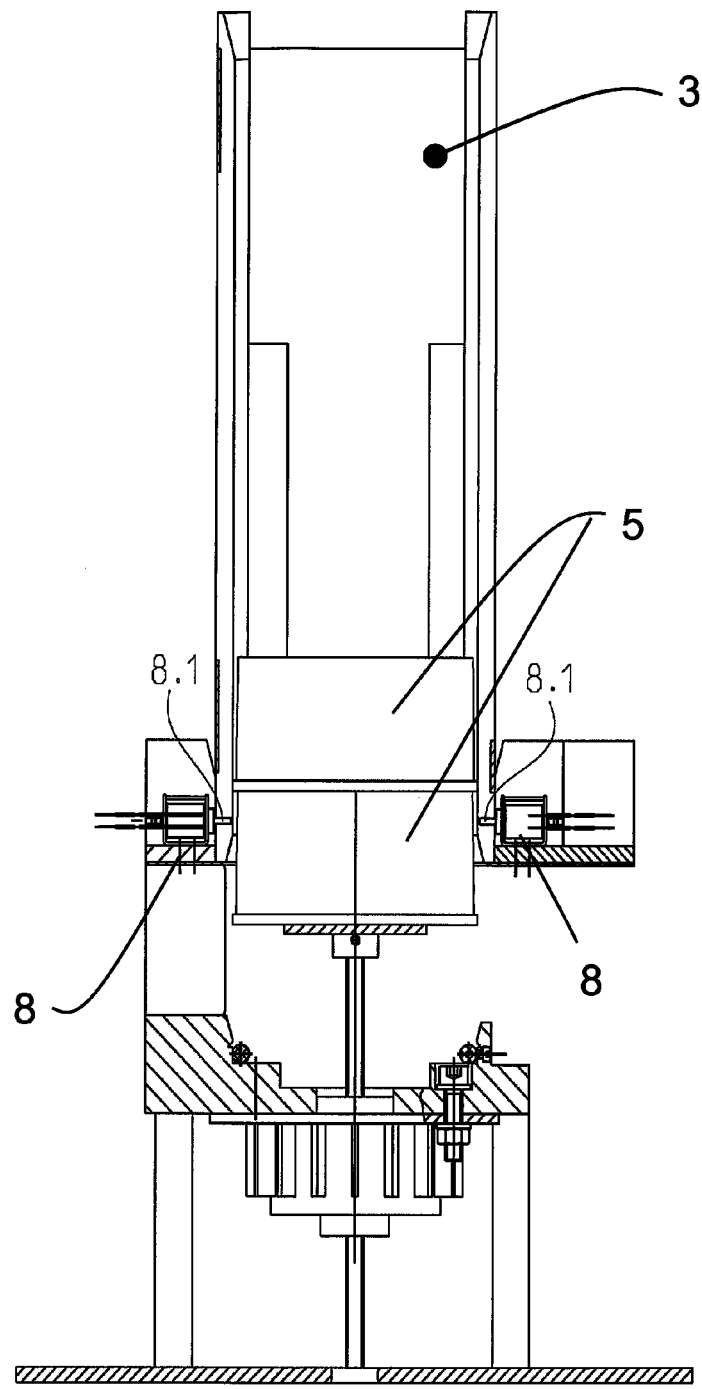
Figure 1D:
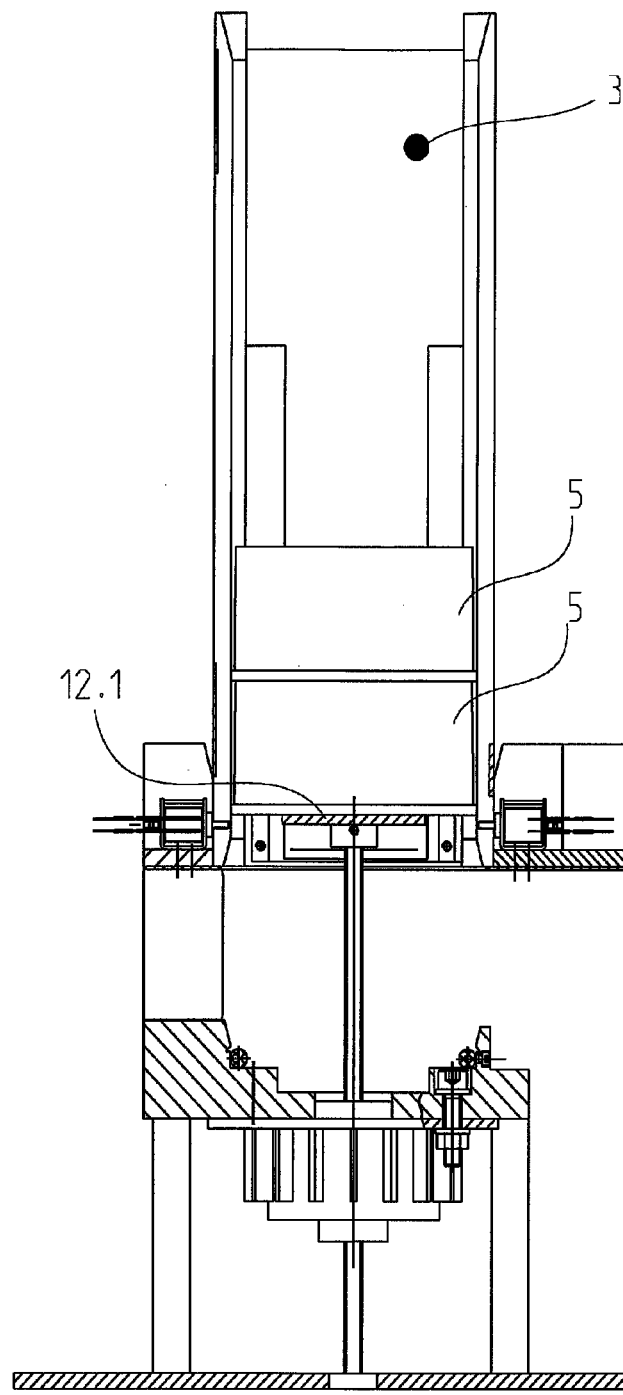
Figure 1E:
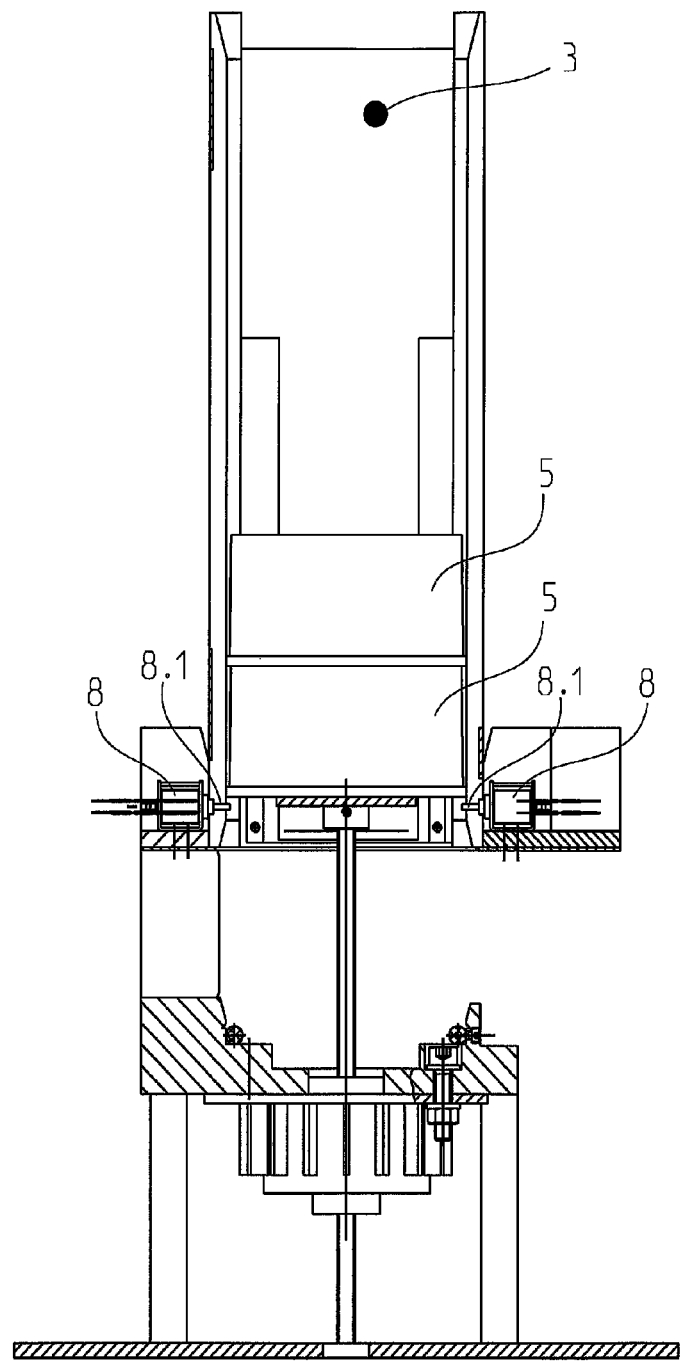
Figure 1F:
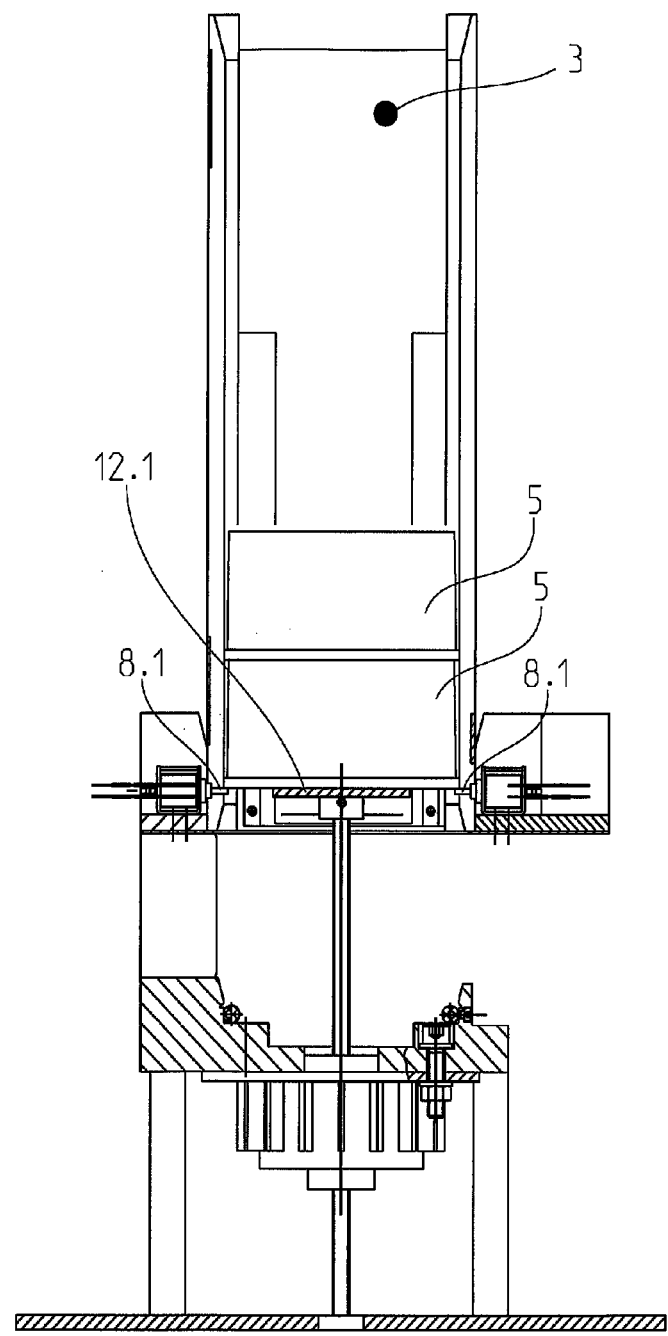
Figure 1G:
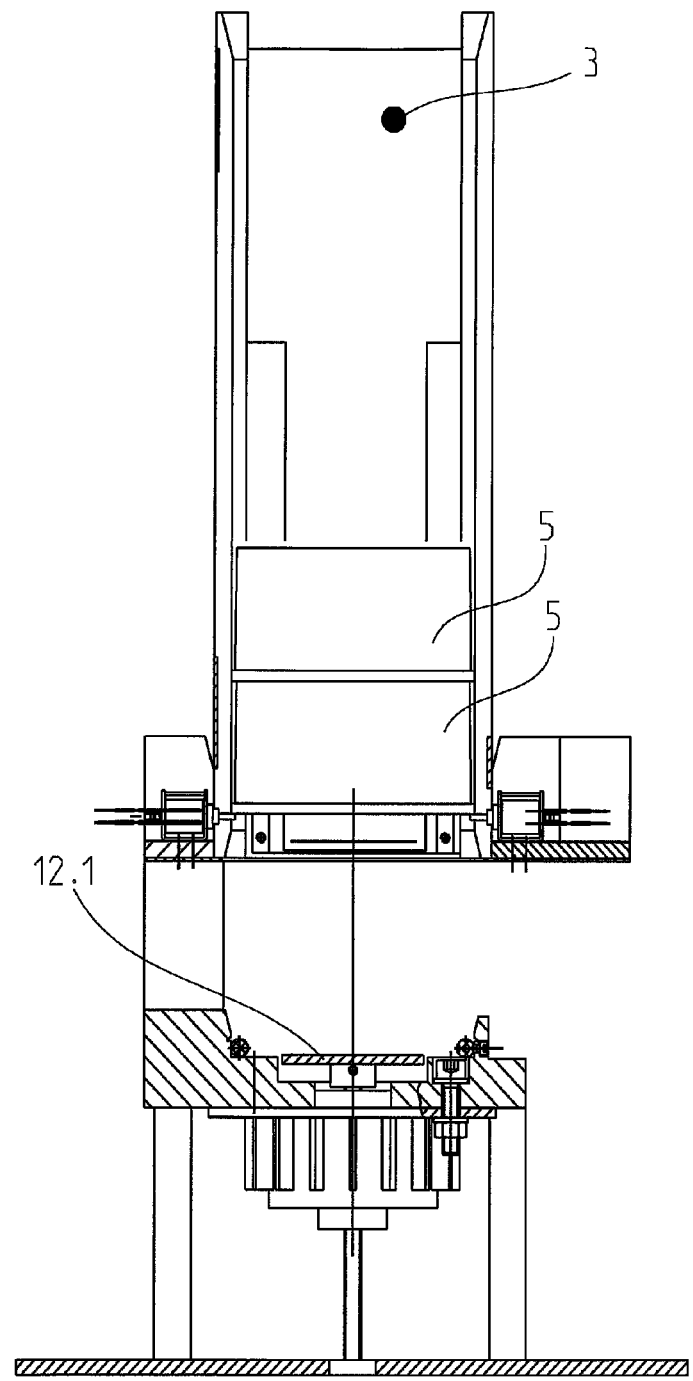
Figure 2:
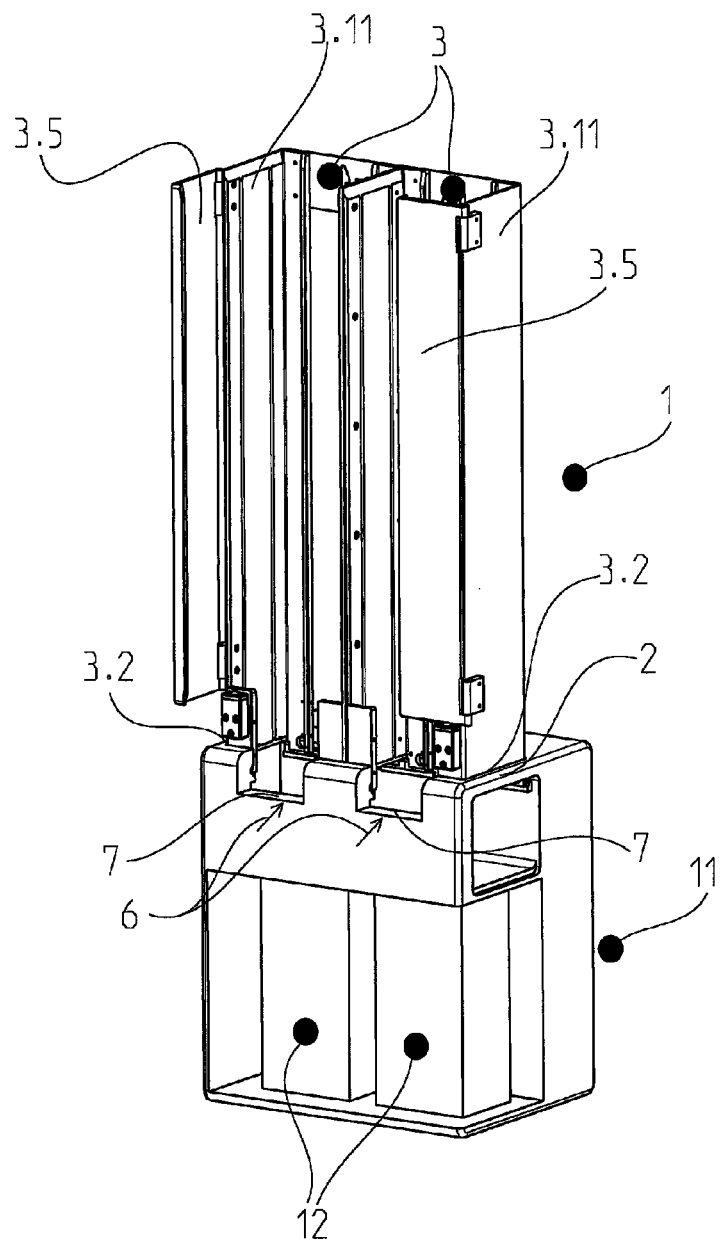
FIG. 2 shows an embodiment of a conventional device for loading, storing and providing objects with standardized dimensions.

In an embodiment, the present invention provides a compact configuration and arrangement of the stackers as well as the possibility of movement to an individual transfer position, whereby only one transfer position is needed for four stackers.

In an embodiment, the present invention provides a device for storing and providing objects having standardized dimensions, in which the objects can be dispensed at short and constant cycle times. Moreover, the device has a high density and is easy to load, even when there is little access space.

The term transfer position of a stacker used below refers to a certain, relative orientation of the stacker along its orbit around the rotational axis. Thus, for instance, an angular position of the stacker can be defined at which an object can be unloaded. Each stacker can be rotated around the rotational axis into the transfer position, whereby the control unit prescribes the direction of rotation and the angle of rotation of each movement. In a preferred embodiment of the device according to the invention, precisely one transfer position is defined for each storage unit.

The presence of only one transfer position per storage unit in each case is greatly advantageous since the unloading device only needs to be moved into a single transfer position. This advantageously makes it possible for the unloading device to be moved at constant cycle times.

The term objects with standardized dimensions preferably refers to microplates, racks for pipette tips and the like as well as auxiliaries and equipment employed in a laboratory furnished and operated according to the state of the art.

The stackers, which according to the above-mentioned SBS standard have a rectangular free cross section, are not all arranged radially in the same manner as is commonly the case in a carrousel, but rather they are arranged compactly around the rotational axis. In a preferred embodiment, as seen from above, a square having a free central area is formed by the stackers. In a top view of the stackers, corresponding points of the elevations of the stackers are each situated on a shared orbit. Such an inventive compact arrangement of the stackers allows quick rotational movements around the axis of rotation. Owing to the arrangement close to the axis, the centrifugal forces and—due to the inertia of the storage unit—the requisite acceleration forces during a rotation around the rotational axis are kept small, making it possible to achieve short movement times and small dimensions of the drive as well as low energy consumption. Moreover, substances or substance mixtures contained in the objects such as solutions or specimens are not greatly accelerated, which helps to markedly reduce detrimental effects such as, for instance, when the solutions spill over from the individual wells.

The stackers can be configured, for example, as a hollow profile. In at least one wall of each stacker, there can be slits or closeable openings, for instance, doors, through which the stacker can be loaded. The walls can also be reduced, for example, to two diagonally opposite corner areas. Combinations of the above-mentioned configurations are likewise possible.

The carrier plate can be any suitable flat element made of many possible materials such as, for example, plastics, metals, metal alloys or composites. Elements such as a ball bearings or a roller bearings that ensure a low-friction rotation of the storage unit around the rotational axis can be present in or on the carrier plate along an interface between the carrier plate and the substructure. Moreover, means are present on the interface or at another place of the carrier plate by means of which a directed force can be transmitted to the carrier plate in order to generate the rotational movement. Such means can be non-positive, positive or positive/non-positive couplings.

Preference is given to an embodiment of the device according to the invention in which the carrier plate is connected to a drive for generating a rotational movement of the carrier plate around the rotational axis, and the drive, in turn, is connected to a control unit in such a way as to conduct signals.

It is also advantageous for the carrier plate to be configured in such a way that it can be reversibly placed onto the substructure, along the lines of a module, in other words, it can be separated from the substructure and placed back onto it. This translates into an easy and flexible loading and configuration of the device according to the invention.

It is likewise advantageous for the stackers to be reversibly joined to the carrier plate. The stackers can be, for instance, magazines that can be removed manually or automatically. Such a configuration means that individual stackers or all of the stackers, depending on the applicable operating conditions, can be quickly replaced with stackers that have different dimensions, for example, a larger capacity, or that are loaded with different objects. Moreover, the stackers can be loaded outside of the device, after which the loaded stackers can be easily placed into the storage unit.

The substructure can be configured, for example, as an open, half-open or closed frame.

An unloading device of the unloading and providing device can be, for instance, a suitable gripping, clamping or hoisting system. The providing device can be, for example, a conveyor belt, a conveying platform or another suitable conveying system.

In a simple embodiment of the device according to the invention, the unloading and providing device is arranged in such a way that an object can be unloaded and subsequently dispensed from a stacker that is in the transfer position. In other embodiments, the unloading device and even the providing device can be moved in the direction of at least one of the axes of a Cartesian coordinate system.

The unloading and providing device can be configured in such a way that a prescribed orientation of the unloaded objects can be established when they are dispensed. In particular, these objects can be rotated by a specific or freely selectable angular position. For instance, an object, irrespective of its orientation in the stacker at the transfer position, can be dispensed in the portrait format, in the landscape format or at another angular position, as desired.

In a refinement of the device according to the invention, the stackers are configured in such a way that the objects are stacked in them one above the other. The carrier plate has openings that correspond to bottom surfaces of the stackers and, for each stacker, there is a separation device for purposes of separating the lowermost object from the objects above it. There is a lifting device to vertically raise and lower the objects of a stacker, and the unloading device is arranged in the substructure below the transfer position so that an object can be moved through the carrier plate.

It is possible for an object to be moved by means of the unloading device through the carrier plate and out of the stacker or else into the stacker.

It is likewise possible for the unloading device to be moved in the direction of the z-axis and for the objects in a stacker to be raised or lowered by the unloading device functioning as the lifting device.

The separation device can be made up of horizontal elements that can extend in a controlled manner and reversibly into the free cross section of a stacker. The objects are stacked on these elements.

The separation device can be made up of at least two movable latches arranged on opposite sides of the stacker, and a stack of objects present in the stacker rests on these latches. The latches can be controlled and moved, for example, mechanically, magnetically, pneumatically or hydraulically.

The latches are particularly advantageous when a stacked upper object and a lower object are touching each other at a contact surface that is made up of the top surface of the lower object and the bottom surface of the upper object, and the extension of the contact surface on at least two opposite sides is smaller than the bottom surface of the object stacked thereon. As a result, (peripherally) next to the contact surface, a depression is formed into which the latches can engage in such a way that the objects stacked thereon rest on the latches and are held in place. This is the case, for example, with microplates according to U.S. standard ANSI/SBS 2-2004 "Footprint Dimensions" for microplates whose bottom surface is larger on all sides than the top surface.

The separation device can also consist of at least two clamping chucks arranged on opposite sides of the stacker, so that objects present in the stacker can be clamped between the clamping chucks. Such a configuration is advantageous when the contact surface is only slightly smaller, of the same size or larger than the bottom surface of the upper object. This is the case, for instance, when the objects are microplates with lids.

Moreover, there can also be combinations of separation devices such as, for example, the simultaneous arrangement of movable latches and clamping chucks. These can also be actuated jointly or independently of each other, as a result of which the device can be employed for various types of objects (microplates, racks for pipette tips).

Individual elements of the separation devices can also be configured so that their height can be adjusted, thus allowing vertical raising and lowering of the objects in a stacker by means of these elements functioning as the lifting device.

Another conceivable configuration of the device according to the invention exists when the stackers have horizontal storage compartments to store objects, and the unloading device can be moved parallel to the z-axis, so that specific objects can be unloaded from the storage compartments (random access) by means of the unloading device. An unloading device that can be moved parallel to the z-axis can be a lifting mechanism having a horizontally swiveling conveying platform.

In a refinement of the device according to the invention, several storage units are arranged on a baseplate so as to be uniformly distributed around a central axis that is perpendicular to the baseplate. The storage units located on the baseplate form an array of storage units. The baseplate is located between the carrier plates of the storage unit and the substructure.

It is extremely advantageous for the baseplate to be configured so that it can rotate around the central axis. As a result, it is possible to move the individual storage units into positions that allow easy loading of the stackers. With this approach, several storage units can be used on one baseplate, even under conditions that are tight or that only allow limited access.

The storage units are preferably arranged so close around the central axis that this array of storage units occupies the smallest possible footprint while the carrier plates of the individual storage units can nevertheless rotate freely around their corresponding rotational axes. As a result, the forces needed for the rotation around the central axis are kept small.

Such an array of storage units has at least one of the above-mentioned unloading and providing devices. In a preferred embodiment, an unloading device is present that can be moved underneath the carrier plate along an x-y plane parallel to the carrier plate and can be brought to the transfer position of each stacker.

It is possible to re-define the transfer positions after the baseplate has been rotated around the central axis, as a result of which the movement distances of the unloading device can be optimized. Then, there is no need to move the various storage units back to their original position.

It likewise falls within the scope of the envisaged objective for at least one storage unit of an above-mentioned device according to the invention to be arranged in a chamber and for the chamber to be selected from among a group comprising climate controlled cabinets, gassing chambers, irradiation chambers, cooling chambers and freezing chambers, as well as combinations thereof.

It is also possible for an array of storage units to be arranged in a chamber.

Moreover, it is possible for the storage units to be arranged as a plurality of storage units on both sides along a passage, and for the transfer position of each stacker on the passage to be defined.

The device according to the invention can be configured in such a way that objects can be loaded into the stackers at constant cycle times at one end of the stacker, as a result of which, every time a new object is loaded into the stacker, each object is moved towards the other end of the stacker and the object is unloaded when it reaches the other end of the stacker, so that all of the objects are held in the stacker for the same length of time. In other words, the object is pushed through the stacker stepwise (one step per cycle). In this process, the order in which the objects were loaded into the stacker is retained. This principle of loading and unloading is referred to as "first in, first out" (FIFO).

Operating the device according to the invention on the basis of the FIFO principle advantageously allows standardized chemical or biochemical processes in the objects to take place for the same duration for all of the objects. Such processes can be, for example, incubations (e.g. digestion, restriction and/or ligation) of biological specimens.

It is also possible for the design of the device according to the invention to allow a number of objects to be loaded into the stacker in a certain sequence, and for the loaded objects to be unloaded from the stacker in the opposite order, so that the objects are present in the stacker for different periods of time. This principle of loading and unloading is referred to as "last in, first out" (LIFO).

In order for an object to be unloaded from a stacker of a storage unit and then dispensed, the control unit and the drive serve to move the stacker to the transfer position. The unloading device moves to the transfer position and approaches the stacker from below.

Depending on the configuration of the device, the stack of objects, except for the at least one object that is to be unloaded, is raised and held by means of the lifting device. The elements of the separation device are removed from the free cross section of the stacker, as a result of which the object can be released and unloaded by the unloading device through the carrier plate where it can then be dispensed by the providing device.

It is likewise possible for the elements of the separation device to be unloaded from the free cross section of the stacker, while the stack of objects is held by clamping and lowered by a certain amount that corresponds approximately to one stacked object, and the elements of the separation device once again extend into the stacker and into the stack of objects above the object to be unloaded. Once the clamping is released, the lowermost object is discharged.

It is also possible for objects to be moved by means of the unloading device through the carrier plate and into a stacker that has been moved to the transfer position. In this process, the above-mentioned steps are carried out in the reverse order.

In a first mode of operation of the device according to the invention, one stacker of each storage unit is empty, while the other three stackers of a storage unit are full of objects. Objects are unloaded one after the other from a full stacker and dispensed to another unit, for instance, a pipetting system. Once the object in question has been processed, for instance, filled, by the other unit, the thus processed object is loaded into the empty stacker by means of the unloading and providing device. In this manner, a full stacker can be emptied while, at the same time, an initially empty stacker is filled.

If there are several storage units, each storage unit can have an empty stacker. It is also possible that there is only one empty stacker in the entire array of storage units.

It is likewise possible for all of the stackers to be full and for the unloaded objects to be taken to another unit, from where they are not conveyed back to the storage unit or to the array of storage units.

Figure 3:
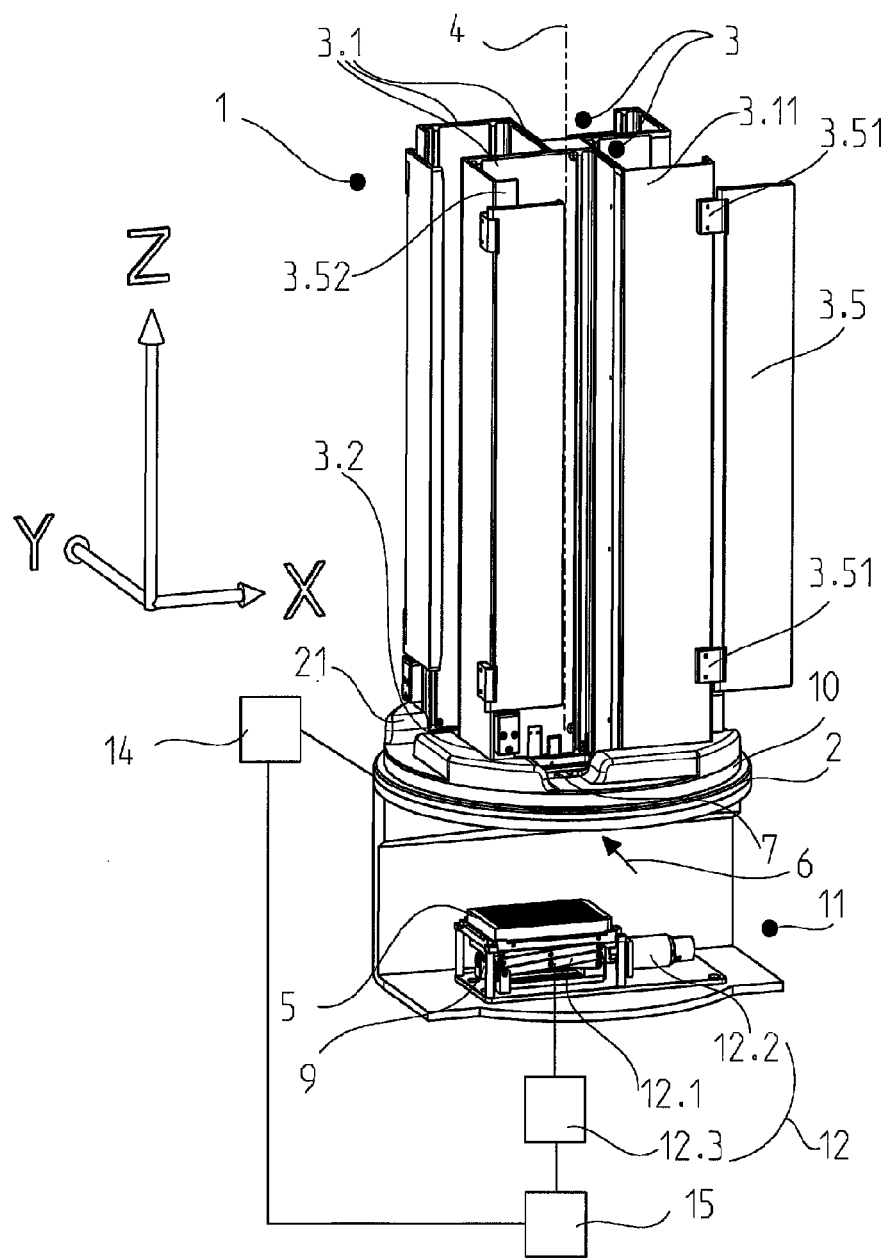
FIG. 3 shows a perspective view of an embodiment of a device in accordance with the invention.

The device according to the invention entails the advantage that a large number of objects can be stored within a very small space, while nevertheless, these objects can be unloaded and dispensed quickly and flexibly from the stackers.

providing An embodiment of the device according to the invention is shown in FIG. 3 and it comprises a storage unit 1 having a carrier plate 2 on which four stackers 3 are arranged symmetrically centered around a rotational axis 4, each offset with respect to each other by an angle of 90°; a substructure 11 with an unloading and providing device 12, a drive 14 and a control unit 15.

The circular carrier plate 2 lies in the x-y plane of a Cartesian coordinate system. The stackers 3 have a rectangular free cross section and are suitable for loading stacks of objects 5 having standardized dimensions according to the U.S. standard ANSI/SBS 2-2004. The stackers 3 are arranged offset with respect to each other by 90°, whereby the U-shaped walls 3.1 of the stackers 3 touch each other in certain areas. Owing to the U-shaped arrangement of the walls 3.1 of the stackers 3, each stacker has an open side oriented towards the outer edge of the carrier plate 2. In the areas where the walls 3.1 of the stackers 3 touch each other, the walls 3.1 are formed by the wall 3.1 of only one of the stackers 3. In other embodiments, the areas where the walls 3.1 of the stackers 3 touch each other can also be formed by the walls 3.1 of both stackers 3.

Due to this configuration of the storage unit 1, each stacker 3 has a free wall 3.11 that does not touch areas of other walls 3.1. A door 3.5 is attached to each of these free walls 3.11 by means of two hinges 3.51 in such a way that, when the door 3.5 is in its closed state, it extends over half the width of the open side of the stacker 3 associated with the appertaining free wall 3.11. In its open state, the door 3.5 is oriented parallel to the free wall 3.11 (see the front, right-hand side of stacker 3). Perpendicular to the free wall 3.11, there is a stop 3.52 that protrudes into the open side of the stacker 3, that serves to guide the objects 5 in the stacker 3, and that limits the movement of the door 3.5 in the direction of the free cross section of the stacker 3. On its free lengthwise edge, the door 3.5 has a projection in the direction of the open side of the stacker 3, whose length corresponds to the thickness of the stop 3.52

In other embodiments, the door 3.5, the type, number and arrangement of the hinges 3.51 as well as of the stop 3.52 can all be configured differently. In particular, the door 3.5 can be present on a free end wall 3.11 of a stacker 3 and, in its closed state, it can extend over half the width of the open side of an adjacent stacker 3. The walls 3.1 can also be configured differently or else reduced in size. It is likewise possible for no doors 3.5 to be present.

The carrier plate 2 has openings 7 whose shape, position and size match bottom surfaces 3.2 of the stackers 3.

The storage unit 1 is placed reversibly and positively onto the substructure 11 along an interface 10. This interface 10 has a peripheral flat surface on which a ball bearing ring installed in the bottom of the carrier plate 2 rolls. A peripheral edge that projects perpendicularly upwards from the flat surface is configured so as to match a groove in the carrier plate 2, so that the storage unit 1 is secured on the substructure 11 against unintentional movement in the x-y plane.

The drive 14 that is connected to the control unit 15 so as to conduct signals is located on the interface 10, and the action of the drive causes the storage unit 1 to be rotated around the rotational axis 4 in a controlled manner. A cover 21 to protect the interface 10 and the means contained in there is placed onto the carrier plate 2.

An unloading device 12.1, which is a component of the unloading and providing device 12, is arranged under the opening 7 that is located in a transfer position 6. The unloading device 12.1 is connected to a drive 12.2 as well as to a providing device 12.3, which is likewise a component of the unloading and providing device 12, in such a way that the unloaded object 5 is transferred from the unloading device 12.1 to the providing device 12.3 so that it can be dispensed by the latter. The unloading device 12.1 is combined with a lifting device 9 by means of which the unloading device 12.1 can be moved in the direction of the z-axis.

Figure 4:
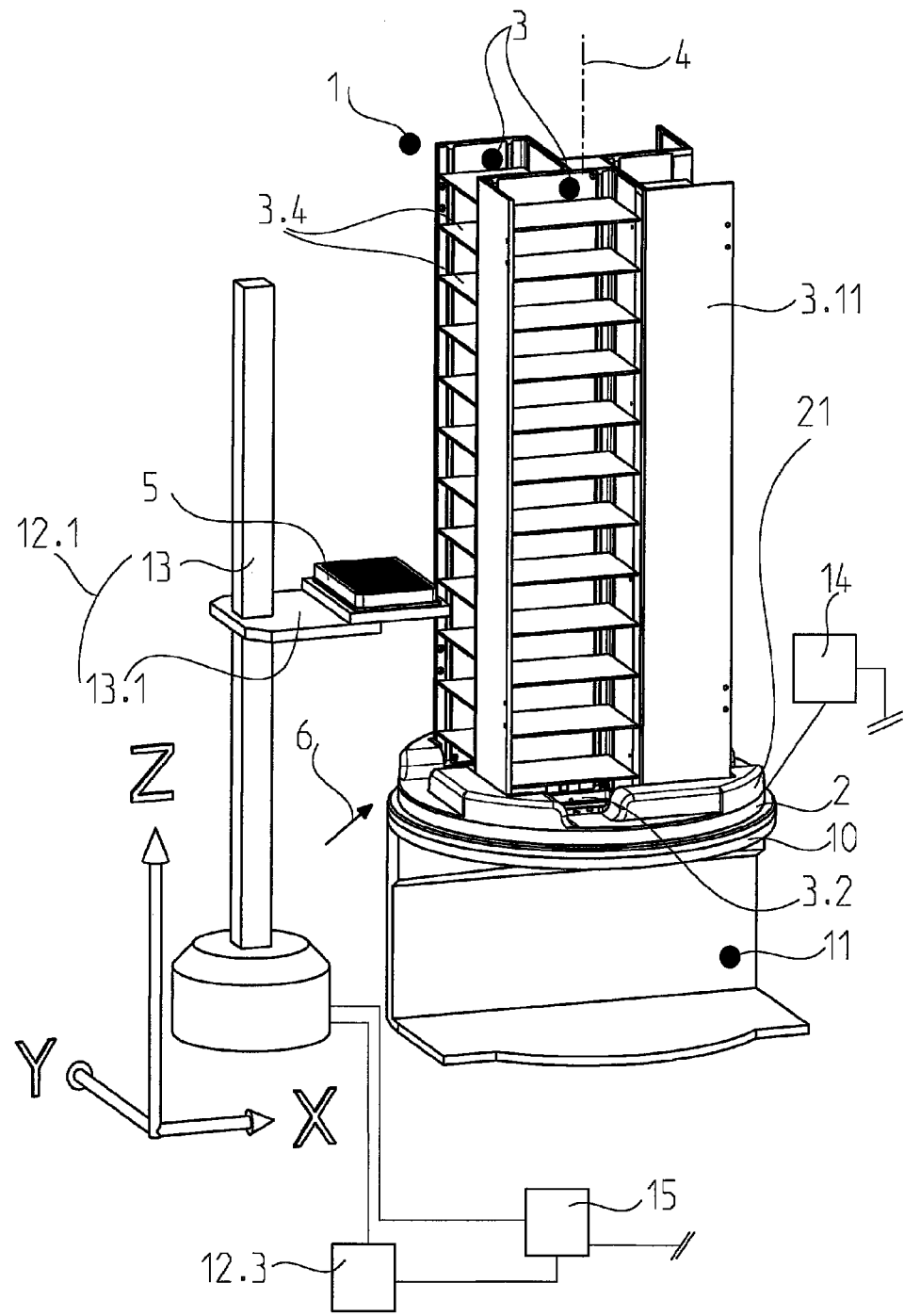
FIG. 4 shows a perspective view of another embodiment of a device in accordance with the invention.

In another embodiment of the device according to the invention, the stackers 3 as shown in FIG. 4 have storage compartments 3.4 arranged one above the other for purposes of storing objects 5. The carrier plate 2 is configured as described in conjunction with FIG. 3 but without the presence of openings 7. The unloading device 12.1 is configured as a lifting mechanism 13 that is located across from the transfer position 6 and whose height can be adjusted in the direction of the rotational axis 4, and it has a conveying platform 13.1 that can be swiveled to each storage compartment 3.4. A selected object 5 can then be unloaded by means of the unloading device 12.1 from a selected storage compartment 3.4 of a stacker 3 that is in the transfer position 6. The signal-conducting connection between the control unit 15 and the drive 14 of the storage unit is shown as an interrupted line.

Figure 5A:
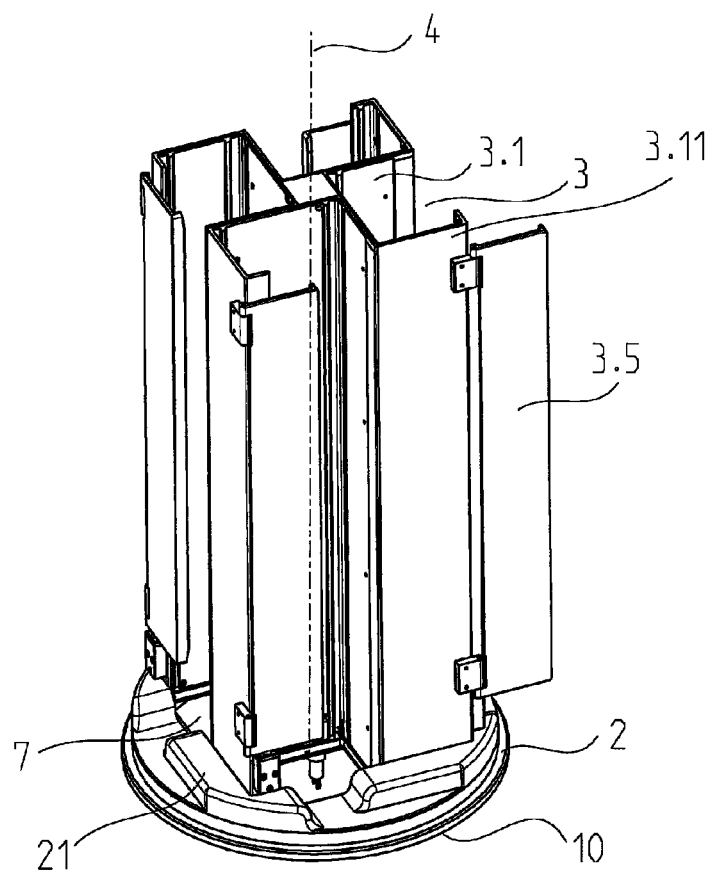
FIG. 5a shows a perspective view of an embodiment of a storage unit in accordance with the invention.

FIG. 5*a* shows an individual storage unit 1 without a substructure 11. The stackers 3 are rotated with respect to each other by 90°, whereby the walls 3.1 of the stackers 3 that are close to the rotational axis 4 touch each other and form a free square around the rotational axis 4. The configuration of the carrier plate 2 corresponds to that described in FIG. 3.

Figure 5B:
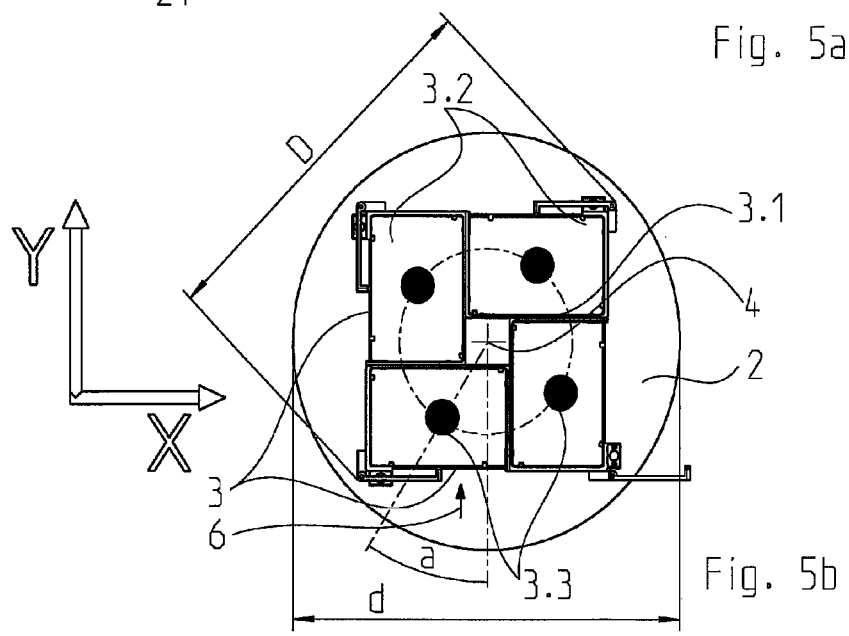
FIG. 5b shows a schematic top view of a storage unit in accordance with and embodiment of the invention.

FIG. 5*b* shows the square basic form of the surface covered by the stackers 3 and their bottom surfaces 3.2 of a storage unit 1. The corresponding points of the elevations of the stackers 3 are each situated on a shared orbit, as is illustrated by a broken line by way of an example for the center points 3.3. of the elevations of the stackers 3.

The transfer position 6 is defined as a relative angular position a of a center point 3.3 of an elevation of a stacker 3 amounting to 45°. An imaginary straight line (drawn as a dotted line) running parallel to the direction of the y-axis of the x-y plane from a traversing point of the rotational axis 4 through the carrier plate 2 serves as the reference to a relative angular position of 0°. The diameter d of the carrier plate 2 here is 320 mm and it is only slightly larger than the diameter D of the storage unit 1.

In other embodiments of the device, another position and another number of transfer positions 6 can be defined.

Figure 6:
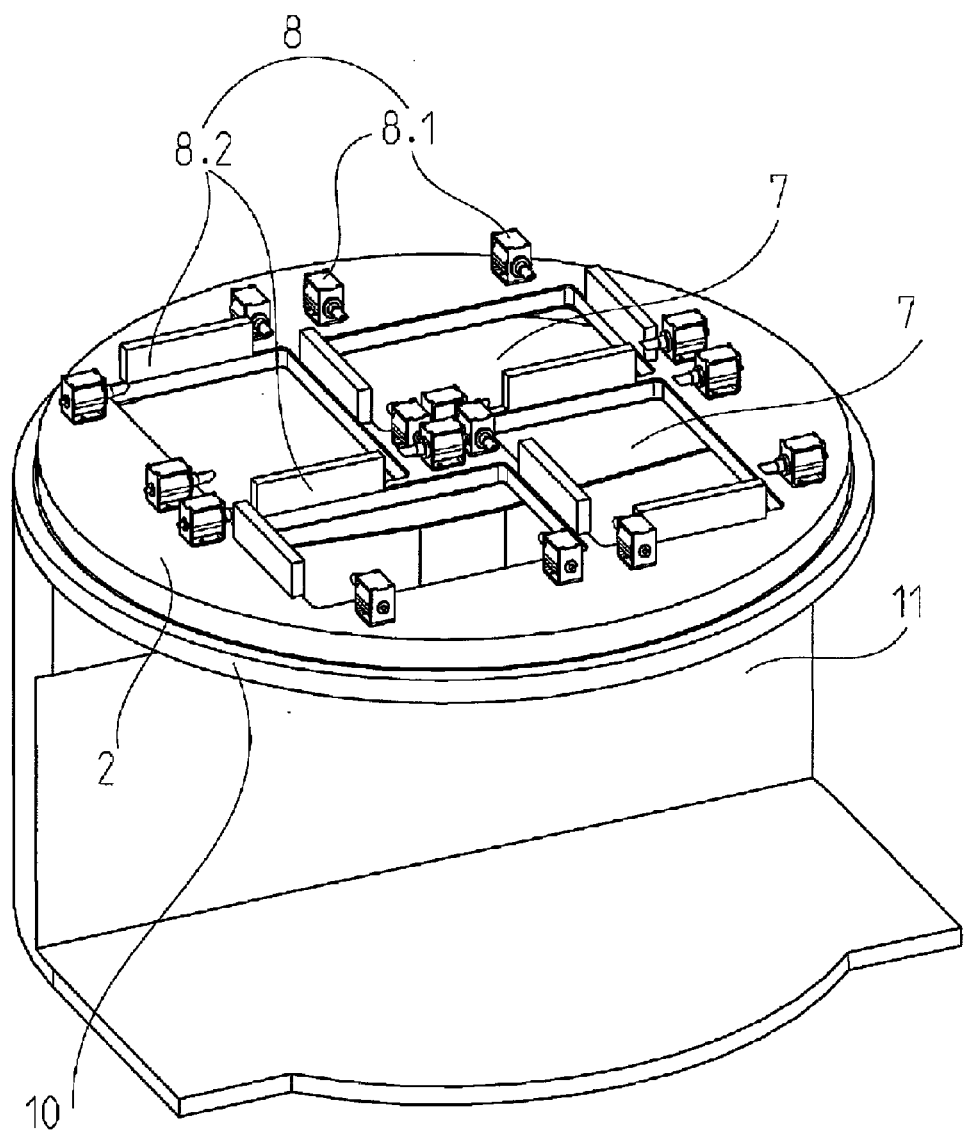
FIG. 6 shows a perspective view of a carrier plate and of a substructure of a device in accordance with an embodiment of the invention.

FIG. 6 shows the carrier plate 2 without stackers 3 and the cover 21. The carrier plate 2 is placed onto the substructure 11 that corresponds to a U-profile lying on its side.

Elements of a separation device 8 are present at the individual openings 7 and these elements extend reversibly into the free cross section of each stacker 3 and are configured as magnetically movable latches 8.1

At the front of each of the openings 7, there is a clamping chuck 8.2 that is configured in one piece and that can be moved into the free cross section of the stacker 3 so that objects 5 located in the area of the clamping chucks 8.2 can be clamped between said clamping chucks 8.2.

In other embodiments, the clamping chucks 8.2 can also consist of multiple parts, they can be arranged differently or be present in a different number. Moreover, the stackers 3 can also be dimensioned for storing objects 5 having other or different standards.

In another embodiment according to FIG. 7, there are several storage units 1 (for the sake of clarity, depicted here without detailed reference numerals) arranged perpendicular and parallel to each other on a baseplate 18. Here, the configuration of the storage units 1 corresponds to the storage unit described in conjunction with FIG. 3. In a first embodiment according to FIG. 7*a*, three identical storage units 1 are distributed uniformly around a central axis 16. The individual storage units 1 can each be rotated around their own rotational axes 4. The individual stackers 3 of the storage units 1 can be loaded from the sides or from above.

In other embodiments, it is also possible for the entire storage unit 1 or for individual stackers 3 to be configured so that they can be replaced by another, optionally new or differently equipped, storage unit 1 or stacker 3.

The embodiment shown in FIG. 7*b* consists of four storage units 1 that are arranged symmetrically centered around the central axis 16. The baseplate 18 can be rotated around the central axis 16 in a controlled manner by means of a drive 19 that is connected to the control unit 15 so as to conduct signals.

The device is housed in a chamber 20 in such a way that the device is only freely accessible from one side (sketched as an open side). The stackers 3 can only be loaded from the open side. For this purpose, the storage unit 1 in question can be brought to the open side by rotating the baseplate 18 around the central axis 16. At the open side, the appertaining stacker 3 is rotated around the rotational axis 4 so as to be brought into a position from which the stackers 3 can be loaded and, in other embodiments, the stackers 3 and/or the storage unit 1 located in that position can be replaced.

The unloading device 12.1 is configured as a planar conveying device 17 that can be moved in a plane below the baseplate 18 that runs parallel to the x-y plane. The unloading device 12.1 is connected to a drive 12.2, and this, in turn, is connected to the control unit 15 so as to conduct signals. For each storage unit 1, precisely one transfer position 6 is defined to which the unloading device 21 can be moved as desired during the operation of the device.

The time needed by the unloading device 12.1 to travel the furthest movement distance determines the cycle time for unloading and providing an object 5.

The movement of the unloading device 12.1 can be delayed by means of the control unit 15 in such a way that the cycle time for unloading and providing an object 15 is constant and independent of the length of the movement distance.

In other embodiments, the unloading device 12.1 can consist of several conveying devices 17. There can also be several unloading devices 12.1.

It is possible to re-define the transfer positions 6 independently of each other after one rotation of the baseplate 18 around the central axis 16, as a result of which the movement distances of the unloading device 12.1 can be optimized.

Figure 8:
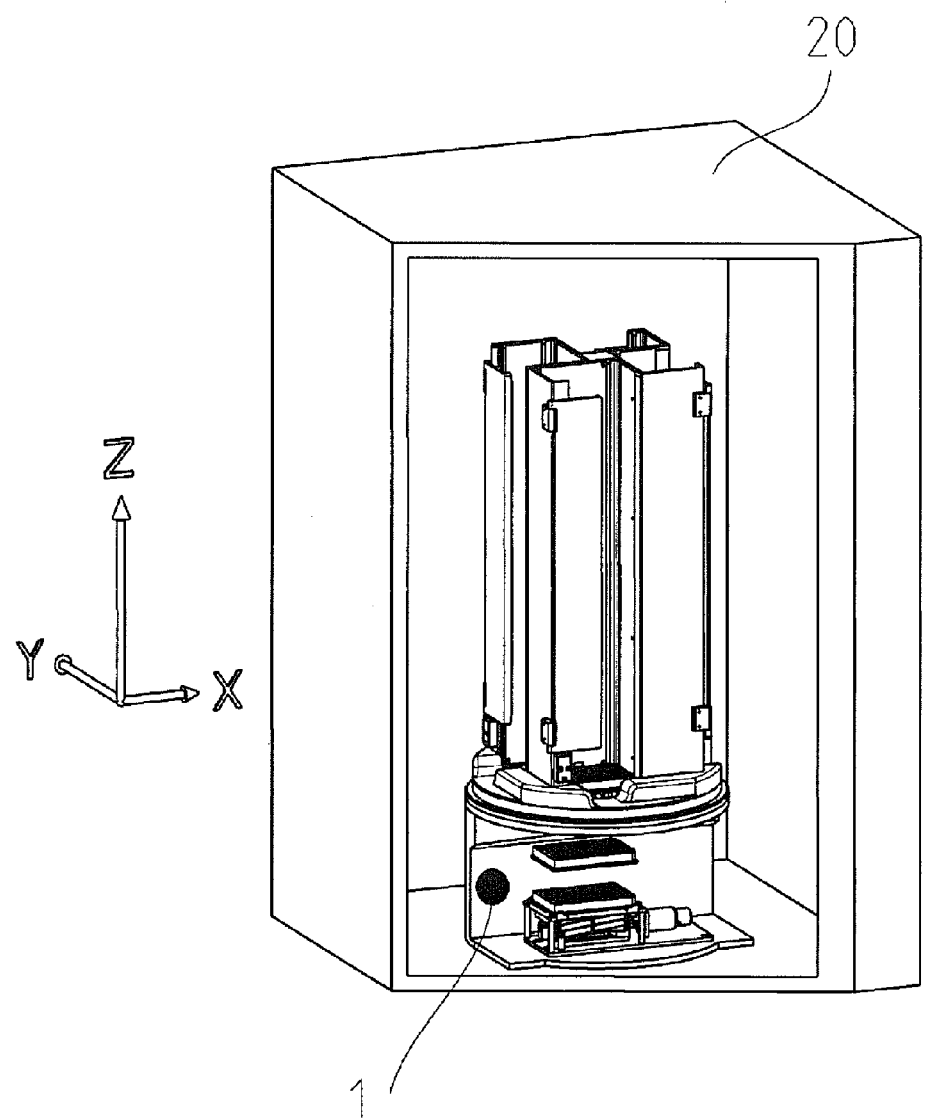
FIG. 8 shows a device according to the invention including a chamber.

In another embodiment according to FIG. 8, a device having a storage unit 1 is arranged in a chamber 20 that is configured as a climate controlled cabinet. The objects 5 are dispensed inside the chamber 20 by the providing device 12.3. In other embodiments, the objects 5 can be conveyed out of the chamber 20 and dispensed outside of the chamber 20.

In other embodiments, the chamber 20 can also contain devices for temperature control (cooling, heating), for irradiation, for gassing and/or for setting a certain pressure.

The device according to the invention can be employed in many technical laboratory applications in the realm of research in molecular biology, biochemistry and molecular genetics as well as in medicine, biotechnology and diagnostics. It allows a very compact storage for a flexible and quick providing of objects that are needed frequently and in large numbers, and it is especially well-suited for being combined with other equipment such as, for instance, pipetting systems, incubators or sterilizers.

The device according to the invention can also be used to load, store and dispense objects having standardized dimensions in places other than laboratories.

While the invention has been particularly shown and described with reference to preferred embodiments thereof, it will be understood by those skilled in the art that various changes in form and details may be made therein without departing from the spirit and scope of the invention.

LIST OF REFERENCE NUMERALS 1 storage unit
2 carrier plate
3 stacker
3.1 wall
3.11 free wall
3.2 bottom surface
3.3 center point
3.4 storage compartment
3.5 door
3.51 hinge
3.52 stop
4 rotational axis
5 object
6 transfer position
7 opening
8 separation device
8.1 latches
8.2 clamping chucks
9 lifting device
10 interface
11 substructure
12 unloading and providing device
12.1 unloading device
12.2 drive
12.3 providing device
13 lifting mechanism
13.1 conveying platform
14 drive
15 control unit
16 central axis
17 conveying device
18 baseplate
19 drive
20 chamber
21 cover
d diameter
D diagonal
a angle

What is claimed is:

1. A device for loading, storing and providing objects having standardized dimensions, the device comprising:
   a storage unit including:
      a carrier plate,
      four stackers each configured to store objects stacked perpendicular to the carrier plate, each of the stackers being configured to receive the objects in a stack in which the objects are stacked one above the other and each of the stackers including a bottom surface disposed on top of the carrier plate, the stackers being disposed symmetrically centered around a rotation axis that is perpendicular to the carrier plate and offset with respect to each other by an angle of 90°, the carrier plate including openings corresponding to the bottom surfaces of the stackers;
   a substructure disposed underneath the carrier plate;
   an unloading device configured to unload a selected object from a first of the stackers that is disposed in a transfer position, the unloading device being disposed in the substructure below the transfer position such that a selected object is unloadable by movement through the carrier plate, wherein the storage unit is rotatable around the rotation axis so as to rotate each of the stackers into the transfer position;
   a lifting device configured to vertically raise and lower the objects disposed in a respective stacker; and
   a separation device corresponding to each stacker and configured to separate a lowermost object in the stack of objects from the respective objects above the lowermost object, the separation device comprising horizontal elements configured to controllably and reversibly extend into a free cross section of a respective stacker including:

at least two movable latches arranged on opposite sides of the stacker and configured to support a respective stack of objects resting on the latches, and at least two respective clamping chucks disposed on opposite sides of each stacker, the respective clamping chucks being configured to clamp objects disposed in the respective stacker between the clamping chucks, wherein individual elements of the separation device are configured to be height adjustable and provide vertical raising and lowering of the objects in the respective stacker so as to function as the lifting device.

2. The device as recited in claim 1, further comprising a drive connected to the carrier plate, the drive being configured to rotate the carrier plate around the rotation axis, and a control unit connected to the drive so as to conduct signals thereto.

3. The device as recited in claim 1, wherein the carrier plate is replaceably removable from the substructure.

4. The device as recited in claim 3, wherein the carrier plate forms a separable module.

5. The device as recited in claim 1, further comprising at least one additional storage unit including a corresponding carrier plate, and a base plate disposed between the substructure and the carrier plates of the storage unit and the at least one additional storage unit, wherein the storage unit and the at least one additional storage unit are uniformly disposed about a central axis that is perpendicular to the baseplate.

6. The device as recited in claim 5, wherein the base plate is rotatable about the central axis.

7. The device as recited in claim 5, wherein the unloading device is movable in an x-y plane that is parallel to the carrier plate and is configured to be movable to the transfer position of each stacker.

8. The device as recited in claim 1, further comprising a chamber, the storage unit being disposed in the chamber, wherein the chamber includes at least one of a climate controlled cabinet, a gassing chamber, an irradiation chamber, a cooling chamber and a freezing chamber.

* * * * *